United States Patent [19]

Galloway

[11] Patent Number: 5,427,738
[45] Date of Patent: Jun. 27, 1995

[54] METHOD AND SYSTEM FOR DETOXIFYING SOLID WASTE

[75] Inventor: Terry R. Galloway, San Leandro, Calif.

[73] Assignee: Synthetica Technologies, Inc., Richmond, Calif.

[21] Appl. No.: 225,438

[22] Filed: Apr. 8, 1994

Related U.S. Application Data

[63] Continuation of Ser. No. 27,360, Mar. 8, 1993, abandoned.

[51] Int. Cl.$^6$ ............................................. B01J 10/00
[52] U.S. Cl. ................................... 422/26; 422/111; 422/120; 422/173; 241/23; 588/229
[58] Field of Search ................. 588/229-230; 423/DIG. 18; 241/23-24; 422/26, 111, 173, 120

[56] References Cited

U.S. PATENT DOCUMENTS

| | | | |
|---|---|---|---|
| 4,688,495 | 8/1987 | Galloway | 588/230 |
| 4,863,702 | 9/1989 | Galloway | 422/111 |
| 4,874,587 | 10/1989 | Galloway | 422/189 |
| 4,884,756 | 12/1989 | Pearson | 241/99 |

OTHER PUBLICATIONS

Lauer et al. "Chemical Engineering Techniques", Reinhold pub. corp., 1952, pp. 119-121.

*Primary Examiner*—Lyle A. Alexander
*Attorney, Agent, or Firm*—Coudert Brothers

[57] ABSTRACT

A method and system for detoxify hazardous waste is described. The waste is mechanically particularized to a predetermined particle size and is then subjected to a gas flow having a temperature between 250° C. and 750° C. At the same time, the particularized waste is agitated to enhance its exposure to the gals flow, resulting in gasification of a substantial portion of the solid waste. The remaining particularized waste residue is collected for recycling of further disposal. After passing through the agitated particularized waste, the gas flow is circulated to a thermolytic detoxification reactor and then recirculated to the agitated particularized waste.

12 Claims, 3 Drawing Sheets

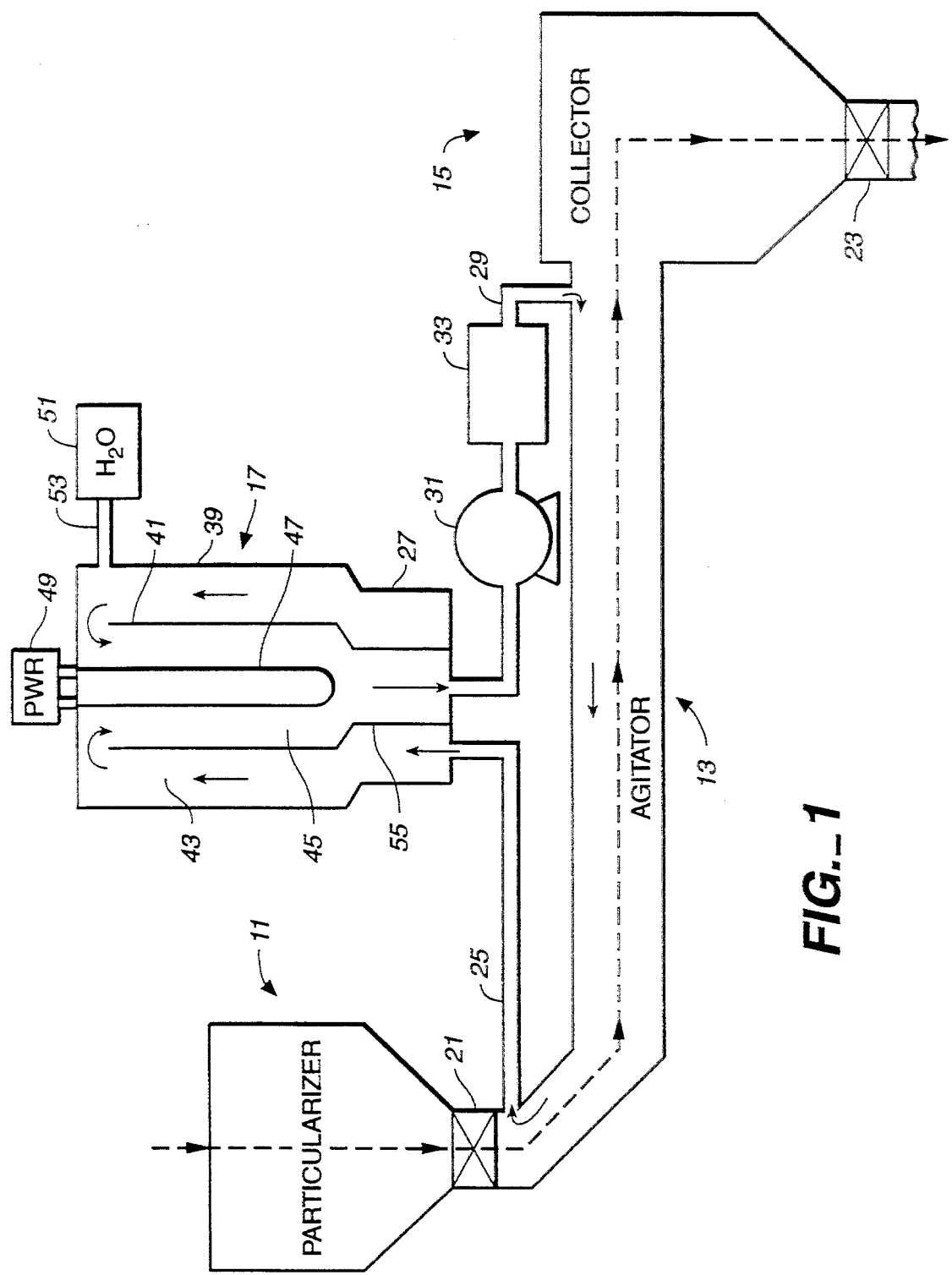
FIG._1

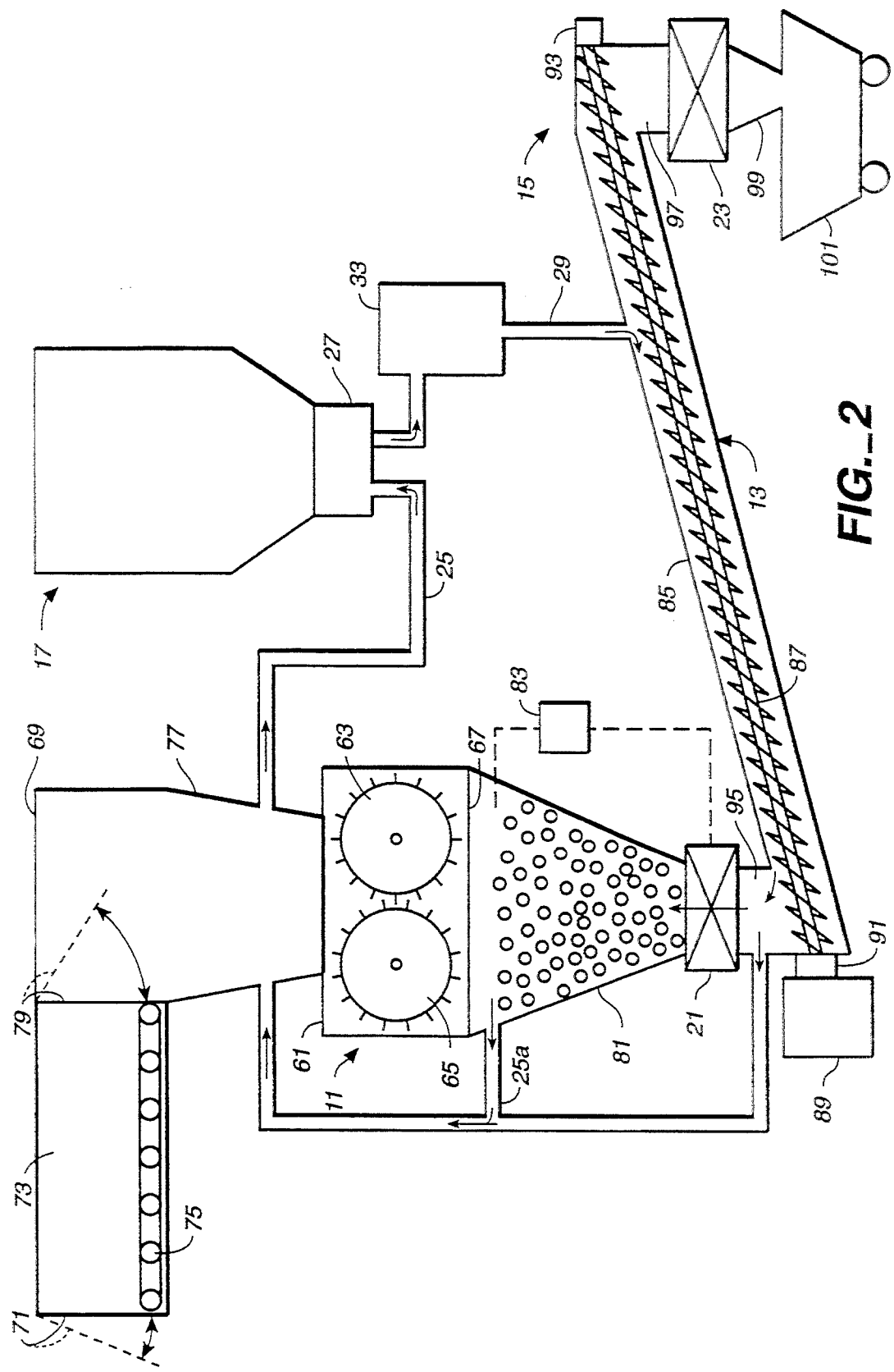
FIG._2

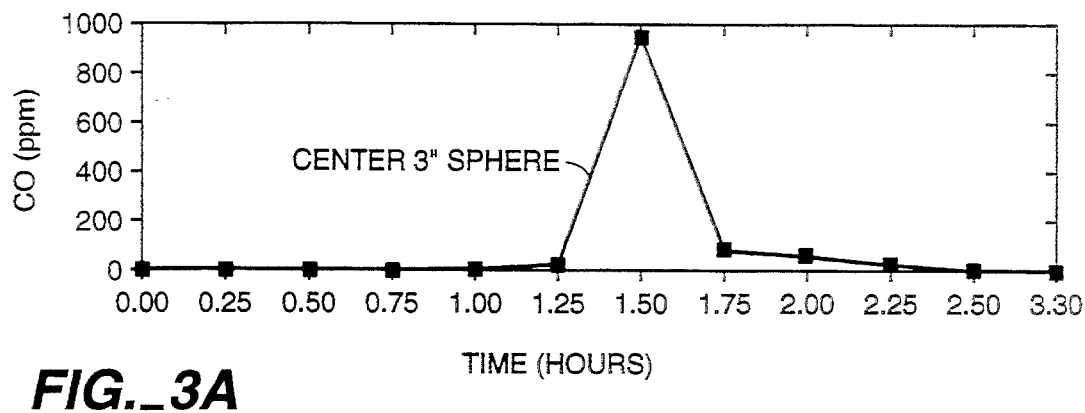
FIG._3A
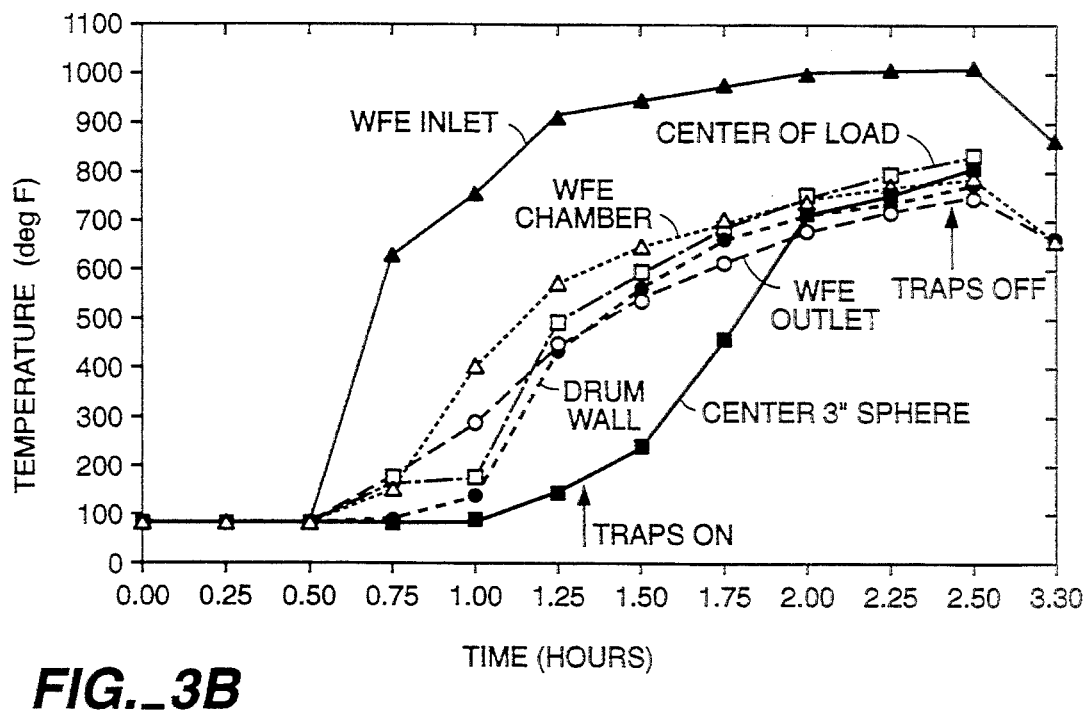
FIG._3B

METHOD AND SYSTEM FOR DETOXIFYING SOLID WASTE

This application is a continuation of application Ser. No. 08/027,360 filed Mar. 8, 1993 now abandoned.

This invention relates to the detoxification of hazardous waste. More particularly, the invention relates to an improved method and system for detoxifying solid waste using a thermolytic detoxification reactor.

BACKGROUND OF THE INVENTION

The detoxification of hazardous waste such as certain organic compounds, medical waste contaminated with pathogens, and low level radioactive waste, is an ongoing problem for many industries. The shipment of such waste to disposal sites creates significant danger of environmental release in the event of an accident, and the volume available as landfill sites is rapidly disappearing while costs are increasing rapidly. Accordingly, there is a need for methods and systems to efficiently dispose or reduce the volume of such toxic waste at the site where the waste is generated.

The use of incinerators for burning hazardous waste is becoming unacceptable. Incinerators that meet current air pollution laws and have efficient operation tend to be relatively large and therefore may not be economically feasible for placement at facilities where toxic waste is generated. Moreover, incinerators are often difficult to control and create strong community and political ill-feeling. Perhaps more importantly, however, the incineration process may produce other toxic products which are themselves undesirable and which are difficult or impossible to eliminate.

In U.S. Pat. No. 4,874,587, issued Aug. 26, 1987 and assigned to the assignee of the present invention, a process and apparatus are described for hazardous waste detoxification which represent a significant improvement over incinerators. In the aforesaid patent, a reactor is described in which toxic destruction levels of 99.99% or more are achieved. The aforesaid process and apparatus are operated without air or free oxygen reaction and produce an effluent gas which is primarily comprised of carbon dioxide, hydrogen, and water. The process and apparatus described in the aforesaid patent has been classified by the United States Environmental Protection Agency as "thermolytic detoxification" as differentiated from "incineration".

A thermolytic detoxification reactor operates to react a gaseous stream of toxic material with water in excess of the stoichiometric amount necessary to react with substantially all of the organic compounds in the stream of toxic waste. This reaction is carried out at a temperature in excess of about 250° C. and results in an effluent gas stream of high temperature comprised primarily of carbon dioxide, water, and hydrogen but also containing low levels of carbon monoxide. The latter can be readily converted to carbon dioxide by catalytic oxidation.

Since the principal reaction in a thermolytic detoxification reactor occurs in the gas phase, the processing of liquid and semi-solid waste, where the waste material can be relatively easily gasified, is fairly straightforward. For example, a system for vaporizing and gasifying toxic waste for feeding to a thermolytic detoxification reactor wherein the toxic waste is liquid contained in a metal drum is shown and described in U.S. Pat. No. 4,863,702, issued on Sep. 5, 1989 and assigned to the assignee of the present invention. In the case of solid waste, however, conversion of the waste into a gaseous form for feeding to a thermolytic detoxification reactor is not as straightforward as in the case of liquids and semi-solids. Melting, incineration or direct gassification of such solid materials prior to feeding into the thermolytic detoxification reactor may be possible for some materials. However, for many materials proper preparation would necessitate a totally separate additional system based on a different technology, substantially increasing capital expense and energy cost.

Accordingly, it is an object of this invention to provide an improved method and system for detoxifying solid toxic waste.

Another object of the invention is to provide an improved method for detoxifying solid toxic waste which employs a thermolytic detoxification reactor and which is adaptable to on-site applications.

Still another object of the invention is to provide an improved method and apparatus for detoxifying solid toxic waste which minimizes environmental hazards in the feeding of the waste, the processing of the waste, and the disposal of residues.

Other objects of the invention will become apparent to those skilled in the art from the following description and accompanying drawings.

SUMMARY

Very generally, the method and system of the invention contemplate detoxifying the solid medical waste by first mechanically particularizing the waste to a predetermined particle size. Thereafter, the particularized waste is subjected to a gas flow of a hot gas at a temperature in excess of about 250° C. and less than about 750° C. At the same time, the particularized waste is agitated to enhance its exposure to the hot gaseous flow for a period of time sufficient to gasify a substantial portion of the solid waste. Thereafter, the remaining particularized waste residue is collected for recycling or further disposal. After passing through the agitated particularized waste, the gas flow is circulated to a thermolytic detoxification reactor wherein the toxic components in the gas stream are reacted with water in excess of stoichiometry to produce a hot and substantially harmless effluent gas. The effluent from the reactor is recirculated as the gas flow to which the particularized waste is subjected while being agitated.

DESCRIPTION OF THE DRAWINGS

FIG. 1 is a schematic diagram illustrating the general configuration of the method and system of the invention;

FIG. 2 is a schematic diagram illustrating a preferred form of the invention as it applies to the processing of medical waste; and FIG. 3 is a set of graphs portraying the results of a test of the system of the invention without employing agitation and with certain test materials and particle sizes.

DETAILED DESCRIPTION

The general nature of the method and system of the invention may be more specifically discerned from FIG. 1. The system of the invention comprises four major components: a particularizer 11, an agitator 13, a collector 15, and a thermolytic detoxification reactor 17. The path of the solid material through the system is indicated by the dashed arrows extending from the particularizer 11 through the agitator 13 to the collector 15. The solid arrows indicate the flow of the gas stream through the agitator 13 to and from the thermolytic detoxification reactor 17.

More specifically, the solid toxic waste is mechanically particularized in the particularizer 11 to reduce the solid waste to a particle size having a predetermined maximum mean diameter. By mean diameter, it is meant the approximate mean cross-sectional dimension of the particles. It is preferred that the mean diameter be not greater than 4 cm. This may be controlled by any suitable means depending on the specific nature of the particularizer. For example, a shredder or crusher in combination with a screen or cyclone separator may be employed, or a shredder or similar apparatus having a designed particularization level may also be used. Various apparatus for mechanically particularizing solid waste material are well known to those skilled in the art. Examples of such apparatus include spinning knife cutters, size reduction grinders, rotary cylinder cutter shredders, stamping mills, and ball mills.

After the solid waste is particularized in the particularizer 11, it passes into the agitator 13. Preferably, a valve 21 is positioned between the particularizer 11 and the agitator 13 to isolate the two components for confining the gas flow to the agitator 13. The agitator 13 may be any suitable apparatus known to those skilled in the art for providing agitation of the particulate material in order to maximize its exposure to the gas stream. By way of example, the agitator 13 may comprise a fluidized bed, a cyclone reactor, a series of vibrating screens, moving belt, a rotating screw, or a stirred pebble bed reactor.

As will be explained below, however, it is preferred that the agitator 13 be comprised of a rotary screw positioned in an elongated housing for advancing the particulate material in a controlled manner from the particularizer 11 to the collector 15. The agitator is selected to provide exposure of the particularized waste for a length of time sufficient to gasify a substantial portion of the solid waste, preferably substantially all of the toxic components thereof. The specific residence time selected will depend, of course, upon the type of agitator used and the nature of the waste product being processed. Certain materials may take longer to accomplish the necessary purification. Also, the size of the particles may influence the selection of the length of time of exposure of the particles to the gas in the agitator. For most materials, the preferred time of exposure will be in excess of one half hour and less than about five hours.

The collector 15 may be of any suitable configuration in order to collect the particulate residue from the agitator. Preferably, the collector is in communication with the agitator 13 so that evolved gaseous components from the residue in the collector will be drawn into the gas stream and, as explained below, be carried to the thermolytic detoxification reactor 17. Contents of the collector 15 may then be removed through a suitable valve 23 for transport to a suitable disposal site, not shown.

A gas conduit 25 extends, from a location near the juncture between the particularizer 11 and the agitator 13, to the thermolytic detoxification reactor 17. As illustrated schematically in FIG. 1, the lower end of the thermolytic detoxification reactor 17 comprises a heat exchanger 27 by which heat is exchanged between the cooler incoming gas and the hot effluent of the reactor.

A gas conduit 29 carries the reactor effluent back to the agitator 13 at a location which is selected to provide a predetermined path length for the flow of the gas through the particularized material therein. To maintain flow of the gas stream, a suitable blower 31 is provided, shown in FIG. 1 as being located along the conduit 29. Also located along the conduit 29 is a sorber unit 33 which is provided to remove any particularized components entrained in the gas stream in the conduit 29. The sorber unit 33 may comprise one or more beds of adsorbent material such as activated carbon to remove trace organics and metals, and may also contain Selesorb ® to remove any halogens.

The thermolytic detoxification reactor 17 is of the type generally described in U.S. Pat. No. 4,874,587, issued Aug. 25, 1987 and assigned to the assignee of the present invention. The process of thermolytic detoxification involves the reaction, at high temperature, of a gas stream, containing toxic material to be decomposed, with water in the form of super-heated steam. The water is present in excess of stoichiometry and results in the decomposition of 99.99% or more of organic compounds in the gas stream. The effluent gas stream is comprised principly of carbon dioxide, hydrogen and water, with some carbon monoxide. The carbon monoxide may be detected and used as a measure of the extent of decomposition of organic compounds in the reactor. Detection of the amount of carbon monoxide in the effluent gas stream may be accomplished by any suitable means, such as electrochemical specific gas sensors (e.g. Teledyne ®, Sensidyne ®, etc.), ultra-violet spectrophotometric monitors (e.g. Anarad ®, Horiba ®, etc.), and others.

More specifically, the thermolytic detoxification reactor includes a substantially cylindrical housing 39 and a coaxial substantially cylindrical inner wall 41. The cylindrical wall 41 and the cylindrical housing 39 define an outer annular space 43. The cylindrical wall 41 further defines an inner space 45 which communicates with the annular space 43 through an opening provided between the upper end of the cylindrical wall 41 and the upper wall of the housing 39. An elongated U-shaped heating element 47 extends downwardly into the space 45 from a heater power supply indicated schematically at 49. A source 51 of super-heated steam is connected to the reactor 17 via an inlet conduit 53.

At the bottom of the reactor 17, the heat exchanger 27 is provided. A heat exchanger of preferred construction is shown and described in detail in U.S. patent application Ser. No. 685,532 which is incorporated herein by reference. Gas enters the heat exchanger 27 from the conduit 25 and exits the heat exchanger via the conduit 29. Gas entering the heat exchanger passes from the heat exchanger upwardly into the annular space 43 of the reactor 17. Gas exits the space 45 of the reactor 17 through the heat exchanger 27 to the conduit 29. For schematic purposes, a cylindrical heat exchange barrier 55 is illustrated within the heat exchanger 27 and across which the thermal transfer in the heat exchanger occurs. Of course, it will be recognized that this is merely a schematic representation and the more specific details of the preferred heat exchanger are illustrated and described in the aforesaid patent application.

In operating the system schematically illustrated in FIG. 1, solid waste is passed, by suitable means not shown, into the particularizer 11 where it is mechanically particularized to the predetermined particle size. After passing through the valve 21, the particularized material enters the agitator 13. In the agitator, the particularized material is exposed to the gas stream entering the agitator from the conduit 29 and exiting the agitator via the conduit 25. The gas stream is counter in flow direction to the direction of movement of the particularized waste in the agitator 13. During the course of its passage through the agitator, the waste particles are exposed to the hot gas stream. Volatilizable compounds are evaporated and reactive compounds are steam reformed, and are carried off by the gas stream to the thermolytic decomposition reactor 17. This typically effects a net reduction in the volume of the solid material remaining in the agitator 13. At the same time the material in the agitator 13 is heated to a temperature which is sufficient to destroy any pathogens contained in the material, such as might be present in hospital waste material and the like. The gas stream circulating in the thermolytic detoxification reactor 17 is reacted within the reactor to destroy toxic organic compounds. The solid residue is accumulated in the collector 15 and removed through the valve 23, after cooling, for suitable disposal.

Referring now to FIG. 2, a more specific form of the system of the invention is shown schematically. The illustrated system is designed for the destruction of medical waste such as that typically produced by hospitals and clinics. Medical waste typically comprises a variety of materials including plastic, glass, paper, textiles, liquids, metals, and even animal and human bone and tissue. Such materials may carry infectious pathogens, particularly viruses, bacteria, and fungi. In normal U.S. hospital procedures, such materials are collected without segregation in plastic bags with a volume ranging from 0.1 to 0.3 cubic meters. These bags are in most cases red in color and labelled in large letters "INFECTIOUS WASTE" in both English and Spanish. Red bags and boxes are normally picked up by contract medical waste haulers at intervals of from once per day to once every three days. Typically public health regulations prohibit storage of such red-bagged or red-boxed infectious waste longer than ninety-six (96) hours unless it is refrigerated.

Recent public attention has been drawn to the problem of hospital waste as a result of the discovery of such waste washed ashore on public beaches. The transportation of infectious waste from hospitals and clinics to disposal sites, such as incinerators, presents an obvious hazard, particularly in urban areas. Thus, in some instances, autoclaves and incinerators have been used on-site to dispose of such materials. Emissions from incinerators are clearly undesirable in urban areas and landfill disposal of the resultant ash is problematic. Although autoclaves reduce the emissions' problem, the typical high pressure, steam autoclave requires significant cost and experienced labor as a result of the large and potentially risky manual handling operations necessitated. The same large amount of mass of feed material is usually left over after autoclave operations and must be handled and disposed of off-site, usually in landfills. Finally, operating experience with autoclaves has indicated that results vary widely and biological testing must often be done on nearly every load to insure that no live virus enter the landfill and possibly drinking water.

The present invention, when applied to the destruction of infectious waste, offers significant advantages over currently known methods and systems. In particular, thorough heating of the waste material to a high enough temperature to destroy pathogens in the material is readily achieved. Moreover, such temperatures result in the gasification of many other volatile and reactive components in the material, significantly reducing its volume. No harmful emissions result from the process, enabling it to be utilized at many urban sites.

In FIG. 2, components corresponding to similar components illustrated in FIG. 1 have been given identical reference numbers. Thus, the system includes a particularizer 11, an agitator 13, a collector 15 and a thermolytic detoxification reactor 17. These are connected generally as shown and described with respect to FIG. 1 and subject to the qualifications and elaborations set out below. It should also be noted that the fan 31, source of super-heated steam 51, and power supply 49 are not shown in FIG. 2 but should be presumed to be included therein. Similarly, the internal details of the thermolytic detoxification reactor 17 and the appended heat exchanger 27 are not shown, but should also be presumed.

In the embodiment illustrated in FIG. 2, the particularizer 11 comprises a mechanical shredder 61 which includes a pair of rotary shredding drums 63 and 65. These drums rotate in clockwise and counterclockwise direction, respectively, to provide a mechanical shredding of solid waste entering the shredder 61. The configuration of the shredder is such that the waste is shredded in a manner which results in a predetermined particle size. To more closely regulate particle size, a screen 67 may be provided at the bottom of the shredder so that only particles of waste at or below the desired predetermined size will fall from the shredder 61. Preferably, the entire shredder is maintained at a high enough disinfection temperature to prevent the growth of pathogens present in the solid waste and which may become resident in the components of the shredder 61. A suitable temperature for this purpose is at least about 200° C. A shredder suitable for the above described function is available as Model No. 600-E from Shredder Systems, Inc. in Oregon, or Shred-Tech in Colorado.

Infectious medical waste, typically contained in red bags or boxes, is fed into the shredder 61 via a lock-hopper 69. Functionally, the lock-hopper includes an entry door 71 providing access to a first sealed chamber 73. A conveyor 75 is disposed in the first chamber and carries the boxes or bags through the chamber 73 and into an air-lock chamber 77. An air-lock door 79 is provided to isolate the chamber 77 from the chamber 73, thus providing the ability for isolation of the air-lock chamber 77 and shredder 61 from the outside atmosphere. This prevents pathogens from escaping into the ambient atmosphere. When the bags pass through the chamber 73 via the conveyor 77, with the door 71 closed and the door 79 opened, the bags or boxes will fall through the chamber 77 and into the shredder 61 for shredding. It is preferred that the temperature of the internal components of the lock-hopper be maintained at high enough temperature to prevent growth of pathogens on the surfaces thereof. A lock-hopper suitable for use herein is available from most shredder suppliers.

The particularized solid waste produced by the shredder 61 falls into a hopper 81. The lower end of the hopper 81 passes the particulate waste into the agitator 13 via a valve 21. Preferably, the valve 21 is a star-valve such as is available as Model No. 6 from Smoot Company. The level of particulates in the hopper 81 is sensed by a level control 83. The level control causes the valve 21 to pass particulate material once the level of particulate material in the bin or hopper 81 exceeds a predetermined level.

In the illustrated embodiment of FIG. 2, the agitator 13 comprises an elongated sealed tubular housing 85 which is inclined so that the end of the housing 85 adjacent valve 21 is lower than the opposite end of the housing. An elongated feed screw 87 is positioned in the housing 85 coextensive therewith. The feed screw 87 is rotated by a suitable motor drive mechanism 89 and integrity of the housing 85 is maintained by sealed bearings 91 and 93 which support the drive or feed screw 87 for rotation by the motor drive 89. An opening 95 near one end of the housing 85 communicates with the valve 21. An opening 97 at the opposite end of the housing 85 communicates with a valve 23 which is also preferably a star valve similar to that of the valve 21. The conduit 25 communicates with the interior of the housing 85 near the opening 95. A further branch 25a of the conduit 25 communicates with the upper end of the hopper 81. This provides for a branching of the flow of hot gas leaving the housing 85 so that some of the hot gas flows upwardly through the hopper 81. It will be noted that the pitch of the screw varies from one end to the other so that as particulate waste is advanced by the screw toward the opening 97, the consequent reduction in the volume of the waste is accommodated.

The shaft size of the screw 87 is selected to provide sufficient mechanical torque strength to handle the worst case of the waste throughput. This depends on the length of the screw and the rate of rotation and the variation on solids content of the waste. The pitch flight height and shape are also important parameters. The pitch sets the relationship between the mass throughput and the rate of rotation. This also is intimately related to the depth that the waste fills the space between the screw flights. The tighter the pitch the more revolutions of the screw it takes to move the mass through. Also the tighter the pitch for the same shaft rpm, the longer the waste residence time. The extent to which the waste fills the space between the flights determines the degree and extent of the waste mixing and exposure to the hot gas stream. This flight spacing and flight height also affects the degree and amount of turbulence imparted to the gas within the screw cavity that affects the heat and mass transfer between the waste and the flowing gas passing over and past the screw flights.

Considering all of these variables and their interrelationships, a preferred embodiment has a pitch/flight ration of 1:1 (defined as the flight height to flight land length).

Regarding the pitch variation with length, this is important when the reduction in mass or the degree of steam-reforming destruction of the waste as it moves along the length of the screw and is exposed to increasingly hotter and more reactive steam-reforming gas. For wastes with very little inorganic (high steam-reforming destructible content), the volume and mass reduction of the waste along the screw length will be substantial. Thus, the pitch/flight ratio can be reduced to 1:3. This attempts to maintain the waste depth in the space to nearly the same depth as when the waste entered the screw. This method also allows a longer residence time for processing in a shorter (and cheaper) screw length with lower heat load.

The clearance between the screw flight tips and the outer casing provides sufficient space for the hot steam-reforming gas to pass and mix down into the flight cavity for contacting and the reaction with the waste. The spacing must be open enough so that this gas can pass easily without excessive pressure drops. Consequently, we select a spacing of about 3 cm (1.2 inches) at the maximum, with the screw sitting closer to the bottom of the housing with a clearance of 5 mm (0.4 inches). This allows for adequate gas flow for a pressure drop around 5 inches of water. The flow velocity of the gas in the space between the screw tips and the housing is ideally about 50 ft/second. Higher velocity results in excessive pressure drop and slower flow results in poor turbulence, mixing, and heat and mass transfer.

The screw 87 and the housing 85 should be of 316 stainless steel with the screw tips case hardened or hardfaced to guard against excess abrasion and wear. To protect against the especially high temperature and the myriad of gaseous decomposition products that result from the steam-reforming destruction of solid hazardous wastes, stainless alloys such as 316 stainless are preferred.

The screw flights can be smooth or provided with some teeth or flaps that will help lift pieces of the waste up into the gas space to provide better contact with the gas. This helps guard against a lump of waste just moving along the screw without adequate contact with the reactive steam-reforming gas to provide for acceptable destruction of the toxic components. But this kind of surface treatment also runs the risk of catching pieces of plastic and blocking the moving of the waste along the screw.

The housing surrounding the screw is preferably heated to temperatures from 700° to 1400° F. to guard against the deposition of undesirable heavy coke steam-reforming products. These temperatures are needed to insure reaction of the superheated steam with the carbonaceous, coke-like product formation.

The screw inclination with respect to the horizontal is important both for the uniform transport of the waste mass along the screw and also the compactness and simplicity of the mechanical arrangement of the unit on the floor. It is most desirable that the screw be inclined from the bottom of the waste-shreddings feed hooper near the floor up to a height to permit the spent inorganics to pass through a sealed star valve down into a sealed cart. Unfortunately, the incline can cause unstable mass flow of the waste. At angles close to the waste angle of repose can cause some of the waste to roll back under the screw slights in clumps. These clumps can become aggravated as they move along the screw. Clumps of waste will not react with the gas as easily or as well as a uniform loading of waste, thus requiring a longer and hotter screw. A preferred embodiment uses a screw incline of 7° in angle from the horizontal.

The screw can be driven with a hydraulic motor, since such hydraulic hardware may already be available for operating the shredder. This hydraulic system provides particularly high torque and very low rpm, which is particularly difficult for electric motor systems without using expensive and heavy duty gear reductions. Such a drive system provides for variable speed and fast reversals (if necessary to unjam the system) at low cost. The shaft bearings must be particularly heavy to handle the long shaft and torque variations typical in the transport of this waste along the screw at the very high temperatures employed. These bearings must either be externally cooled or mounted externally to provide for natural cooling. A preferred embodiment involves mounting the bearings externally to the screw housing in tubular extensions which are fitted with fins for cooling. The shaft seal should be double with possible gas purging between seals to provide both cooling and to seal against the in leakage of air into the negative pressure regions of the screw.

Of course, there are many more variables that are obvious to those experts in the field of constructing heavy screw feed systems that must operate at especially high temperature, operate with little or no air, and be inert against the myriad of gaseous decomposition products that result from the steam-reforming destruction of solid hazardous wastes.

The hot gas from conduit 29 communicates with the particulate waste in the interior of the housing 85, as may be seen in FIG. 2, along the screw from the conduit 29 to the opening 95. The temperature within the housing 85, as well as the screw 87 linearly declines from conduit 29 to opening 95. And in the region between the conduit 29 and the opening 97, the temperature declines even more rapidly, since no hot gas from conduit 29 flows to the opening 97. Accordingly, the particulate waste in this latter region of the housing is allowed to cool, while at the same time any emitted gases are withdrawn from the region and entrained along with the hotter gas flowing between the conduit 29 and the opening 95. Once reaching the opening 97, the particulate material falls from the housing 85 through the valve 23 into a collection means. In the illustrated embodiment, the collection means is illustrated schematically as a hopper 99 and a wheeled cart 101.

The length of the housing 85 and screw 87, as well as the speed of rotation of the screw 87, will affect the residence time during which the particulate waste is exposed to the flow of hot gas. Also, the speed of rotation of the screw 87 will have some effect on the extent of agitation of the particulate waste in the gas stream. These parameters are all selected, depending upon particle size and the nature of the waste, to achieve the desired degree of detoxification. Such parameters can be readily calculated in accordance with known principles by those skilled in the art to determine a satisfactory set of operating parameters. An agitator employing a feed screw which is satisfactory for use in the invention has the following specifications: 250 mm outside diameter screw by 5 meters in length constructed out of 316 stainless steel, driven by a variable speed motor.

FIG. 3 comprises a pair of graphs designed to show a demonstration of the method of the invention in processing simulated infectious hospital waste. The load of simulated waste was placed into a polyethylene bag which was placed into a fifty-five gallon drum. The top of the bag measured 0.9 meters (twenty-five inches) in height above the bottom of the drum. Within this bag the following solid waste components were distributed:

| 2.3 lbs | sterile bandages | |
| 0.2 | Chloroxl ® bottle | |
| 0.1 | Kaopectate ® bottle | |
| 0.4 | Cloth hospital smock | |
| 0.2 | Face Mask Filter | |
| 0.7 | Polycarbonate plastic bottles | |
| 0.05 | 6 laboratory syringes | |
| 0.5 | Glass bottle | |
| 0.2 | Polyethylene bags | |
| 1.5 | Cardboard boxes | |
| 0.3 | Shredded Wood Packing | |
| 0.5 | Paper | |
| 0.3 | 24 - polyurethane cups | Subtotal = 3.4 kg 7.4 |
| 0.3 | Toluene solvent | |
| 1.0 | Isopropyl alcohol | |
| 0.8 | Methanol | |
| 0.1 | Chlorox ® bleach | Subtotal = 1 kg 2.2 |
| 1.5 | Eveready ® 6-volt dry cell | |
| 3.12 | Hamburger (two 3" (8 cm) spherical balls) | |
| | | Grand Total = 6.5 (14.22 lbs.) |

In under 2 hours nearly one cubic meter of solid waste was reduced some 50 times smaller. The initial weight of 6.5 kg (14.2 lbs.) was reduced to 1.9 kg (4.2 lbs). Temperature profiles within the waste, as shown in FIG. 3, were taken to reveal the temperature transients in the destruction process. It was found that all of the solid waste articles were steam-gasified starting around 315° C. (600° F.) (note CO evolution starting) except for glass, metal, and the interiors of large thermal masses.

The large thermal mass question was designed into the experimental testing program. Large thermal masses (i.e. turkeys cooking in a kitchen oven) must be heated longer to allow for the thermal wave to penetrate from the outside into the central region of the mass. The penetration of this thermal wave is made more difficult when there is internally adsorbed water that must be boiled off before the temperature can rise above 100° C. (212° F.). These effects were the reason that two identical 8 cm (3 inch) spherical balls of hamburger were placed in the center of the load.

Experimentally it was found that the center of the hamburger sphere did not reach 252° C. (270° F.) in thirty-minute time frame (allotted in California's Medical Waste regulations for disinfection), whereas all of the surrounding material did reach 252° C. (270° F.). The center of the hamburger sphere, in fact, only reached 122° C. (140° F.) in thirty-minutes and 212° C. (230° F.) in forty-five minutes. Of the two hamburger spheres, one contained a thermocouple and the other an American Sterilizer Company "Proof Plus" biological indicator containing Bacillus stearothermophilus, as specified in the Title 22 §66845(a)(4)(D) of California's Medical Waste Regs. In addition to the indicator within the hamburger sphere, one other indicator was placed in the load, wrapped in a hospital bandage.

The "Proof Plus" indicator placed within the hamburger sphere never experienced temperatures over 267° C. (285° F.), since the internal glass ampoule, filled with aqueous serum, did not burst (which would occur above 285° F.). The paper label on the indicator also was white and perfectly readable; thus, hot steam did not even contact this paper even for a brief moment. The second otherwise identical hamburger sphere internal thermocouple tended to verify these findings. The "Proof Plus" indicator from the hamburger sphere was then incubated for thirty minutes at 55° C. with a test biological indicator together with a fresh control indicator to see if the Bacillus stearothermophilus spores survived. Both test and control indicator changed from red to yellow, clearly indicating no sterilization. The second indicator placed in the load exceeded 285° F., was sterilized, burst, and was destroyed. This experiment showed clearly the importance of shredding or particularizing (preferably below cm in size) the waste before processing in the.

Gas and particulate matter emissions from this test were far less than anticipated. No detectible particulate material was found to have accumulated on the filter that was run for this purpose. Only low levels of CO were detected almost immediately when hot gas was first passed through the drum of solid waste. Note in FIG. 3, CO levels reached a maximum of around 900 ppm when the load reached around 582° C. (600° F.).

Three vent sample traps were taken during the test shown in FIG. 3, covering XAD2 resin, Molecular Sieve 13Å, and charcoal. Gas chromatography and mass spectrometry measurements indicated the emissions were only benzene, toluene, ethylbenzene, and trichlorofluoromethane, and these were very low. There were no fluorine compounds in the waste (sometimes a freon solvent is used in some plastic or bandages); thus, it is concluded that trichlorofluoromethane was an analytical laboratory contaminant. The benzene, toluene, and ethylbenzene are consistent with the mass of organics (i.e. 6.5 kg or 14.2 lbs) in the infectious waste load. The other two traps showed all organics as "not detectible".

The foregoing demonstration indicates the extent of detoxification of simulated medical waste material without subjecting the material to agitation, as such material would be subjected to in the system of the invention. Accordingly, the system of the invention will provide more efficient processing than was experienced during the foregoing described demonstration.

It may be seen, therefore, that the invention provides an improved method and system for detoxifying solid waste. The method and system of the invention are particularly useful in connection with the processing of infectious medical waste. The system and method of the invention are suitable for on-site applications, thereby significantly reducing environmental hazards arising as a result of transport of toxic solid waste. Moreover, the method and system of the invention result in a net reduction in the volume of the material being processed, making transportation and storage less expensive.

Various other embodiments in addition to those shown and described herein will become apparent to those skilled in the art from the foregoing description and accompanying drawings. Such modifications and further embodiments are intended to fall within the scope of the appended claims.

What is claimed is:

1. A method for decontaminating solid waste containing toxic components in two separate reactors, comprising, mechanically particularizing the waste to a predetermined particle size, thereafter a first reactor subjecting the particularized waste to gas flow which is substantially free of oxygen and which is at a temperature in excess of about 250° C. and less than about 750° C. while agitating the particularized waste in an agitator for a period of time sufficient to gasify a substantial portion thereof and to effect a reduction in mass of the agitated particularized waste remaining in the agitator, thereafter collecting the remaining particularized residue, circulating the gas flow after passing through the agitated particularized waste to a second reactor for thermolytic detoxification of the gas with water, maintaining the ratio of water to toxic components present in said particularized waste is in excess stoichiometry and recirculating the reacted steam-containing effluent from the reactor as the gas flow to which the particularized waste is subjected.

2. A method according to claim 1 wherein the solid waste is particularized by mechanical shredding.

3. A method according to claim 1 wherein the predetermined particle size is less than about 4 cm (1.5 inches).

4. A method according to claim 1 wherein the time period for which the particularized waste material is subjected to the gas flow-while being agitated is in excess of about one-half hour and less than about five hours.

5. A method according to claim 1 wherein the particularized waste is agitated by a rotary screw feeder.

6. A method according to claim 5 wherein the gas flow is circulated through the agitated particularized waste in a direction opposite to the direction of movement imparted to the particularized waste by rotation of the screw.

7. A method according to claim 5 wherein the rotational speed of the screw is controlled in accordance with a measured gas constituent in the effluent from the reactor.

8. A method according to claim 1 wherein the gas flow includes carbon dioxide, carbon monoxide, hydrogen and steam.

9. A method according to claim 1 wherein the particularized waste is agitated by means of a rotary screw, and wherein the speed of the screw is controlled in accordance with a measured constituent of the effluent gas from the reactor.

10. A system for decontaminating solid waste containing toxic components in two separate reactors comprising, means for mechanically particularizing the waste to a predetermined particle size, a first reactor with a agitator means for subjecting the particularized waste to a flow of a gas which is substantially free of oxygen and which is at a temperature in excess of about 250° C. and less than about 750° C. while agitating the particularized waste for a period of time sufficient to gasify a substantial portion thereof and to effect a reduction in mass of the agitated particularized waste remaining in the agitator means, a second reactor carrying out a thermolytic detoxification, means for circulating the gas flow after passing through said agitating means in said first reactor to said second reactor thermolytic detoxification therein with water where the ratio of water to toxic components present in said particularized waste is in excess stoichiometry and means for recirculating the steam-containing effluent from said reactor to said agitating means for reaction with the particularized waste.

11. A system according to claim 10 wherein said particularizing means comprise a mechanical shredder.

12. A system according to claim 10 wherein said agitating means comprise a rotary feed screw.

* * * * *